United States Patent [19]

Schuss et al.

[11] Patent Number: 4,792,304
[45] Date of Patent: Dec. 20, 1988

[54] CATCH MECHANISM FOR A DENTAL HANDPIECE

[75] Inventors: Werner Schuss, Heppenheim; Thomas Bierbaum, Worms, both of Fed. Rep. of Germany; Thomas Muther, Orpund, Switzerland

[73] Assignee: Siemens Aktiengesellschaft, Berlin and Munich, Fed. Rep. of Germany

[21] Appl. No.: 900,619

[22] Filed: Aug. 26, 1986

[30] Foreign Application Priority Data

Aug. 26, 1985 [DE] Fed. Rep. of Germany ....... 3530424

[51] Int. Cl.⁴ .............................................. A61C 1/08
[52] U.S. Cl. .............................................. 433/126
[58] Field of Search ...................................... 433/126

[56] References Cited

U.S. PATENT DOCUMENTS

| 1,355,659 | 10/1920 | Evslin | 433/126 |
| 4,235,595 | 11/1980 | Arnegger | 433/131 |
| 4,255,143 | 3/1981 | Schuss et al. | 433/126 |
| 4,332,562 | 6/1982 | Schuss et al. | 433/126 |
| 4,348,180 | 9/1982 | Schuss | 433/126 |

FOREIGN PATENT DOCUMENTS

| 0029860 | 6/1981 | European Pat. Off. |
| 0029862 | 3/1984 | European Pat. Off. |
| 2756011 | 12/1978 | Fed. Rep. of Germany |

*Primary Examiner*—Robert P. Swiatek
*Assistant Examiner*—Adriene J. Lepiane

[57] ABSTRACT

A catch mechanism for latching a shank of a head housing in a guide sleeve of a grip piece which latch mechanism includes stop surfaces engaged by catch surfaces characterized by an actuation element being carried on the grip part and movable radially inward to shift the catch surfaces from a first position engaged with the stop surfaces to a second position disengaged from the stop surfaces. In one embodiment, the catch surfaces are carried on a shank of the head part and the stop surfaces are on a guide sleeve of the gripping part. In other embodiments, the stop surfaces are provided on the shank of the head part and the catch surfaces are formed by an element carried on the guide sleeve.

24 Claims, 7 Drawing Sheets

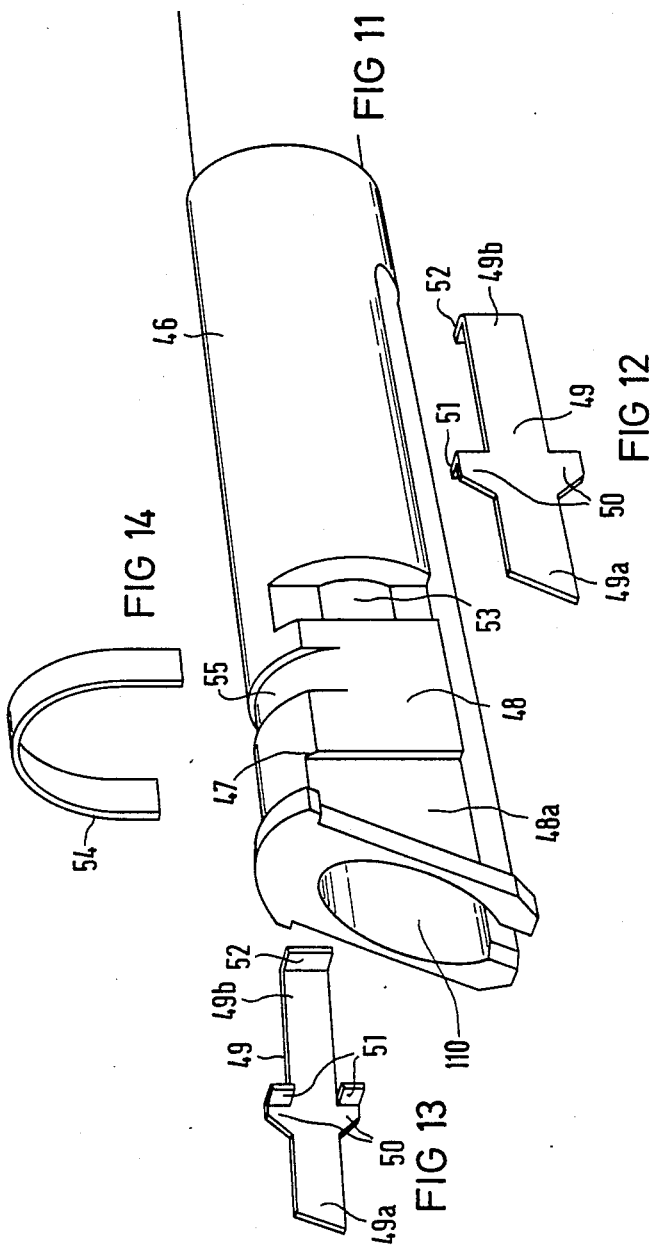

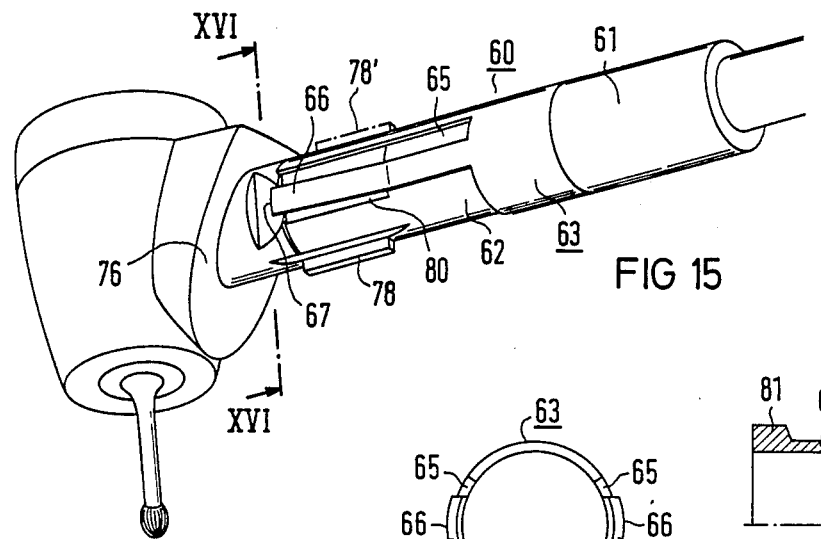
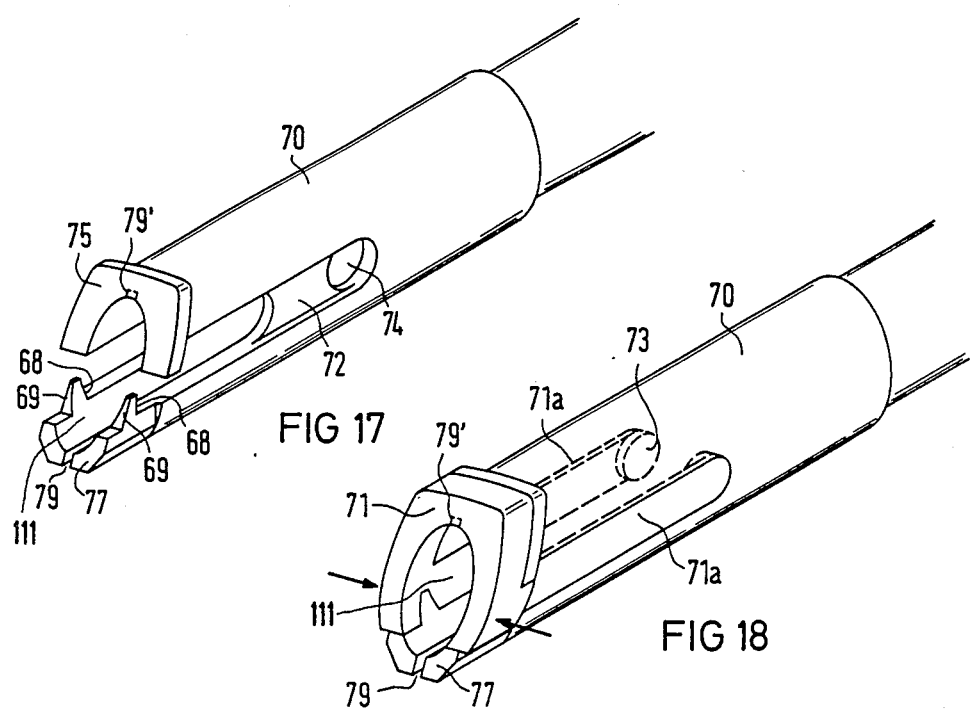

CATCH MECHANISM FOR A DENTAL HANDPIECE

BACKGROUND OF THE INVENTION

The present invention is directed to a catch mechanism for releasably connecting a head part to a gripping part of a dental handpiece. The head part contains a head housing with a neck part terminating in a shank which is received in a guide sleeve of the gripping part and the shank and guide sleeve are provided with anti-twist elements to prevent rotation therebetween. The catch mechanism will include at least one catch element have a radially acting engageable element which is carried by one of the two parts and cooperates with a stop face on the other of the two parts to form a latching connection between the two parts while assembled and the mechanism includes an actuation element for disengaging the catch element from the stop face to enable disassembly.

A radially actuated catch mechanism is disclosed in U.S. Pat. No. 4,348,180 whose disclosure is incorporated by reference thereto and which patent claimed priority from a European application which issued as European Pat. No. 0,029,862. As disclosed in this patent, the neck part of the head part contains a spring-elastic annular sleeve which forms a surface of the handpiece in this region and terminates flush with the surface of the neighboring handpiece parts. Located in a lateral surface region, which is tangential with the head housing, are webs or ridge members which extend parallel to the axis of the annular sleeve and on whose free ends are outwardly directed catch noses or elements which are designed to move radially inwardly and outwardly to engage corresponding recesses in a gripping sleeve. The latch connection can be released in that the head part is grasped with the thumb and index finger in the region of the side edges of the neck part, for example, preferably in the region which is practically tangential with the head housing and are pressed against the annular sleeve. As a result of a deformation of the annular sleeve produced in this way, the catch noses will be disengaged from the locking recesses in the grip part.

In terms of surface, this arrangement of the elastic annular sleeve as well as the webs connected thereto to extend parallel to the axis and having the catch noses, takes a comparably great amount of space. Added thereto is that the sleeve acting as an actuation member forms a relatively large visual surface which must be executed in accordance with the remaining handpiece surface and is, thus, relatively cost intensive.

SUMMARY OF THE INVENTION

The object of the present invention is to provide a catch mechanism having radially movable catch elements which are actuated by an actuation element carried on the gripping part immediately adjacent the head housing. Such an arrangement has the improvements over the hitherto catch mechanism by being produced in a more cost beneficial way.

In the prior art devices, the most cost intensive and largest part of the catch mechnism in terms of surface area is the actuation member which was positioned in the head part. In the present invention, the actuation member is now positioned on the grip part of the handpiece and there are fewer handpieces utilized in the instrument equipment of a dentist relative to the number of head parts and thus, a first cost reduction can be achieved by this improvement. As a result, a shift in the actuation element from the head part to the gripping part moreover, a considerable space saving at the head part itself is achieved and this can be exploited as an advantage for conducting spray and light to the preparation locations. In that the parting location of the head part and the grip part have now been shifted far closer to the head housing in comparison to the prior art structures, additional operating oriented advantages can also be achieved. Although it is now no longer allocated to the head part, the access to the actuation element can occur in the same way as in the known device, namely with the thumb and index finger of the hand grasping the head part, whereby operation is even more favorable because the actuation element already lies directly in the immediate access region of the finger tip of the thumb and index finger when the head housing is grasped with the thumb and index finger. The catch mechanism can, thus, be far more easily actuated. Another beneficial advantage of the arrangement of the present invention is that the cutting edge of the head housing and neck parts offer the finger a certain possiblity for support when the hand piece parts are pulled axially off.

A further cost reduction can be achieved when the catch members with the radially acting engagement means are allocated to the gripping part. Such an arrangement, however, is not to be principly strived for in every case where it can be advantageous under certain circumstances to leave the catch members with the engagement means on the head part because of the fewer catch elements per head part and the lower stress connected therewith.

The catch members of the present invention can have various different designs. A particularly advantageous design can be achieved when catch member and engagement means are fashioned with one or more thin tabs which extend essentially parallel to the axis relative to the hand piece. These tabs have their ends at the face end pressing in a latching fashion against the correspondingly fashioned detent or stops of the other handpiece part which forms the cooperating engagement means and can be disengaged by pressing the actuation member together cause an unlocking radial displacement which occurs towards the inside or outside.

In comparison to radially projecting catch noses, such an end face stop latching requires small installation dimensions because it is practically the wall thickness of the tab that can be fully used for stopping and thus, for latching.

The tabs can be fashioned either inherently resilient or can be arranged radially displaceable by means of an outside spring effect. Further, they can form a multipiece or a single piece catch member. Given the many alternatives, the tabs can be held together by means of a shackle or by means of a sleeve.

Other advantages and features of the present invention will be readily apparent from the following description, drawings and claims.

BRIEF DESCRIPTION OF THE DRAWINGS

FIG. 11 is a perspective view of a third embodiment of the guide sleeve in accordance with the present invention;

FIG. 12 is a perspective view illustrating one side of a third embodiment of a catch member in accordance with the present invention;

FIG. 13 is a perspective view taken from the opposite side of the third embodiment of the catch member;

FIG. 14 is a perspective view of a retaining part for the catch members of FIGS. 12 and 13;

FIG. 15 is a perspective view of a fourth embodiment of a head part with a catch member;

FIG. 16 is an end view of the catch member of FIG. 15 taken from lines XVI—XVI in FIG. 15;

FIG. 17 is a perspective view of a guide sleeve for cooperation with the head part of FIG. 15;

FIG. 18 is a perspective view of a guide sleeve with the actuation element installed thereon; and FIG. 19 is a partial longitudinal cross section of another embodiment of the catch member.

DESCRIPTION OF THE PREFERRED EMBODIMENTS

Figure 1:
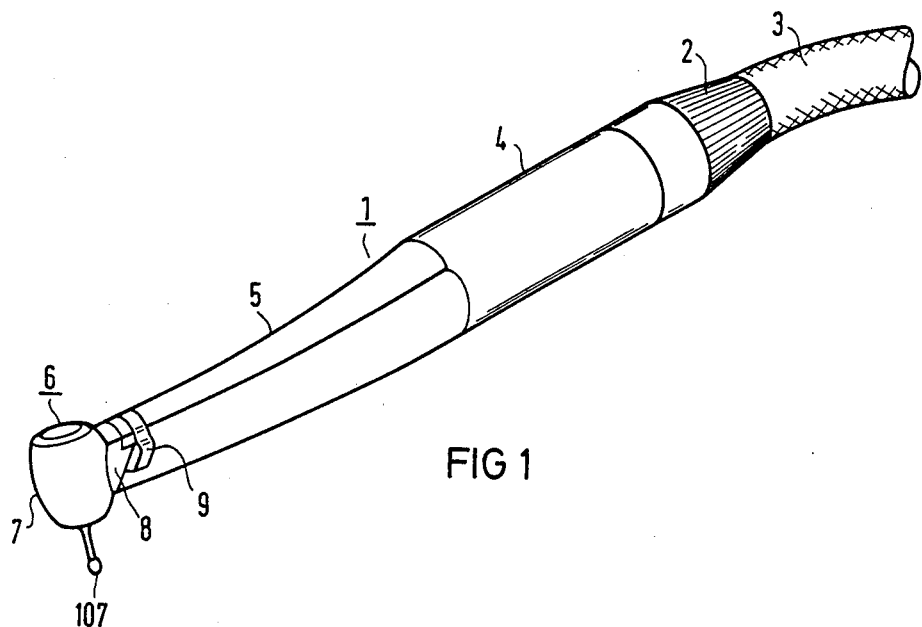
FIG. 1 is a perspective view of a dental handpiece in accordance with the present invention.

The principles of the present invention are particularly useful when incorporated in a dental handpiece 1 of FIG. 1. The handpiece 1 is connected to a supply hose 3 by means of a rotatable connection 2. The handpiece 1 has a hand piece portion 4 which faces the rotatable connection 2 and contains a drive unit (not shown in detail), for example an electric motor or an air motor. A gripping part 5 extends from the handpiece portion 4 and terminates in a head part 6. In a known way, the head part 6 contains a head housing 7 which has a rotatable socket for receiving a tool, such as a burr 107, and has a relatively short neck part 8. In FIG. 1, an actuation element 9 for a catch means for axially latching of the head part 6 relative to the gripping part 5 is illustrated. The catch means will be discussed in greater detail in the following.

Figure 2:
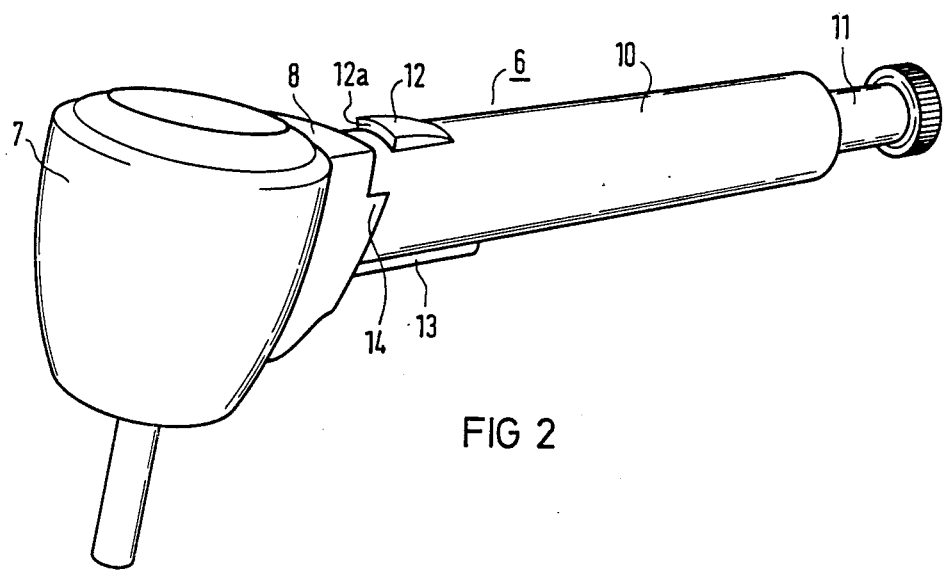
FIG. 2 is a perspective view of a first embodiment of a head part in accordance with the present invention.

The head part 6, as illustrated in FIG. 2, comprises an essentially cylindrical shank 10 in which a drive shaft 11 for driving a tool is rotatably received. A catch nose 12, which comprises a stop face 12a, is located on an upper surface of the shank 10. An anti-twist element in the form of a projection or spline 13 extends parallel to the axis of the shank 7 on an under surface thereof. A relatively short neck part 8 has projections 14 which extend in an axially direction on both sides of the shank so that when the head part is inserted onto the gripping part or gripping piece 5, the projections 14 will provide further anti-twist protection relative to the gripping part, particularly when the catch mechanism has been set.

Figure 3:
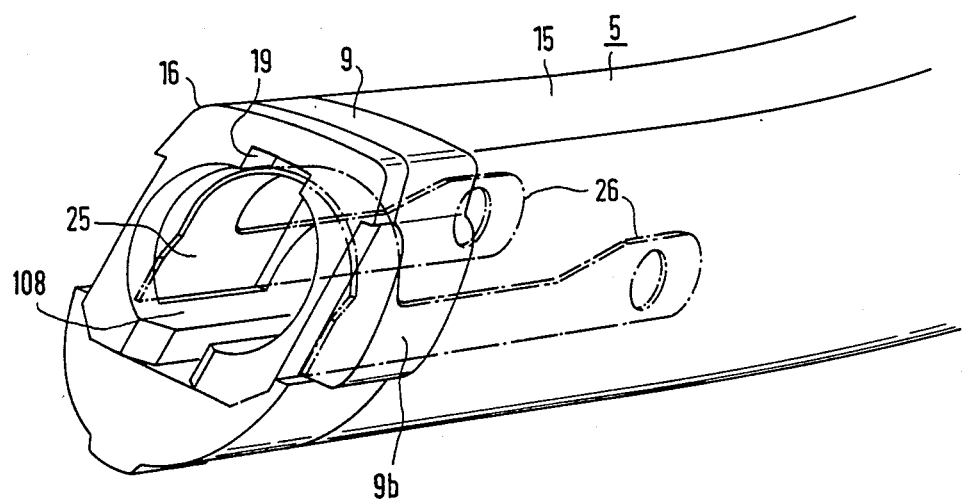
FIG. 3 is an enlarged perspective view of an end of a gripping part of the hand piece of the present invention.

As best illustrated in FIG. 3, the gripping part or piece 5 has an outer sleeve 15 and a guide sleeve 16 is secured in the sleeve 15 and has an axial bore 108 for accepting the shank 10 of the head part 6. As illustrated, the sleeve 15 provides a space for receiving the actuating element 9.

Figure 5:
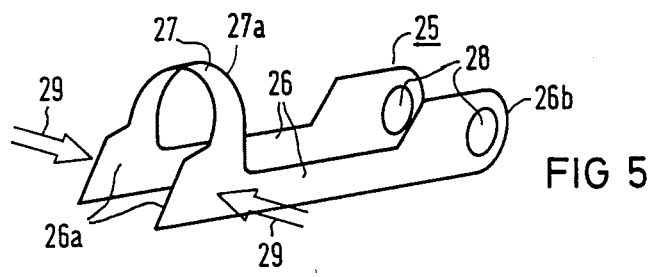
FIG. 5 is a perspective view of a first embodiment of a catch member for the head part.
Figure 4:
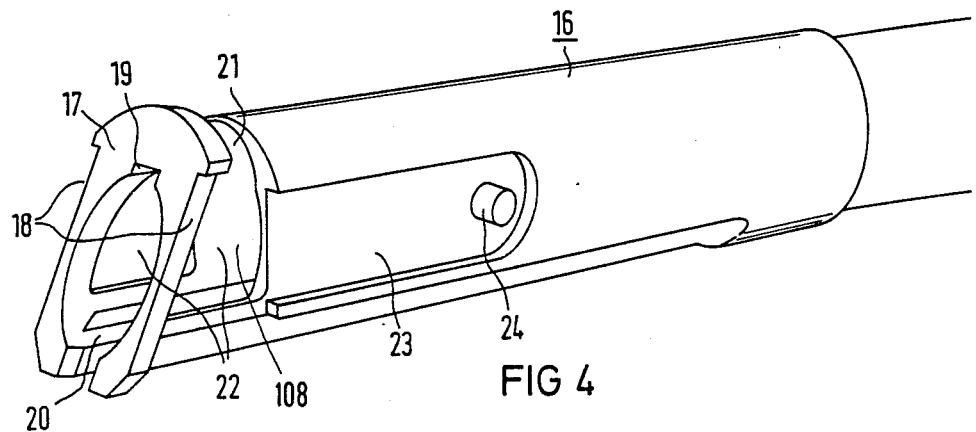
FIG. 4 is a perspective view of a first embodiment of the guide sleeves securable in the gripping parts.

As shown in FIG. 4, the guide sleeve 16 is substantially a cylindrical guide sleeve having a slanted end face 17 facing the head part 6 and has a milled out portion 18 at both sides into which the projections 14 of the neck part 8 are received when the head part is assembled in the guide sleeve 16. A groove 19 is provided on the upper surface of the bore of the sleeve to allow an unimpeded passage for the catch nose 12 which is situated on the upper surface of the shank 10 of the head part 6. A longitudinal slot 20 lying diametrically opposite to the groove 19 represents a cooperating member for the anti-twist element 13. The guide sleeve 16 also contains a milled or turned portion 21 which extends over roughly half of the shank circumference and provides a cut through over half of the diameter of the guide sleeve. This turned out portion or cut 21 forms clearances or spaces 22 which are provided on both sides. In addition, the sleeve 16 has outer recesses 23 on both sides which extend parallel to the axis and include fastening pins or projections 24 for the acceptance and holding of the catch element 25 which is illustrated in FIG. 5.

The catch or member 25 is formed by two strip-shaped sections or elements 26 extending roughly parallel to the axis which are connected to one another adjacent one end 26a by means of a shackle 27 and which have acceptance bores 28 for the pins 24 at the other ends 26b. The catch member 25 is composed of a spring material which is resilient and forms pressure faces in the region of the transition from the shackle 27 to the end sections 26a which pressure faces are referenced by the arrows, such as 29 in FIG. 5. The catch member 25 is slipped over the turned out portion 21 of the sleeve 16 so that the two lateral resilient sections 26 are fixed in the grooves or recesses 23 with the pins 24 being received in the bores 28. In the mounted condition, the pressure faces overlie the regions of the spaces 22. After insertion of the catch member 25, the actuation element 9, which is a discrete part, is slipped onto the guide sleeve 16 from above. The part 9 is fashioned as a roughly U-shape with two legs 9a and 9b. This part is preferably composed of plastic and is resilient. As a result, the two legs, which form actuation keys, project slightly from the generated surface of the hand piece on both sides. The catch member 25 can be deformed in the region of the pressure faces when the legs 9a and 9b are radially pressed together, for example with the thumb and index finger of the hand embracing the hand piece 1, so that the original hemispherical or semi-circular shape of the shackle 27 is deformed upwardly to such a degree that when the head part 6 is axially withdrawn, the catch nose or stop surface 12a is disengaged from the shackle 27 and the catch nose can slide under the shackle 27.

It should be evident from viewing FIGS, 1 and 3 that the catch mechanism, which is in its assembled condition, has the shackle 27 assuming its semi-circular configuration with an edge 27a engaging the stop surface 12a of the catch nose 12 to form a latch condition and hold the head part in the gripping piece. When the legs 9a and 9b of the element 9 are compressed radially inward, they urge the ends 26a of the resilient section together to bow the shackle 27 upward and out of engagement with the stop surface 12a and thus, into an unlatching condition. In this manner, the head part 6 can be easily withdrawn from the gripping piece 5.

Figure 7:
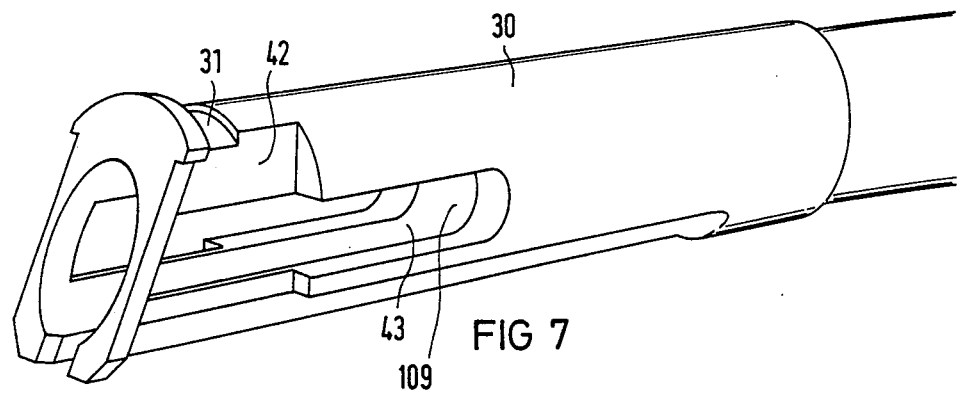
FIG. 7 is a perspective view of a second embodiment of a guide sleeve.
Figure 8:
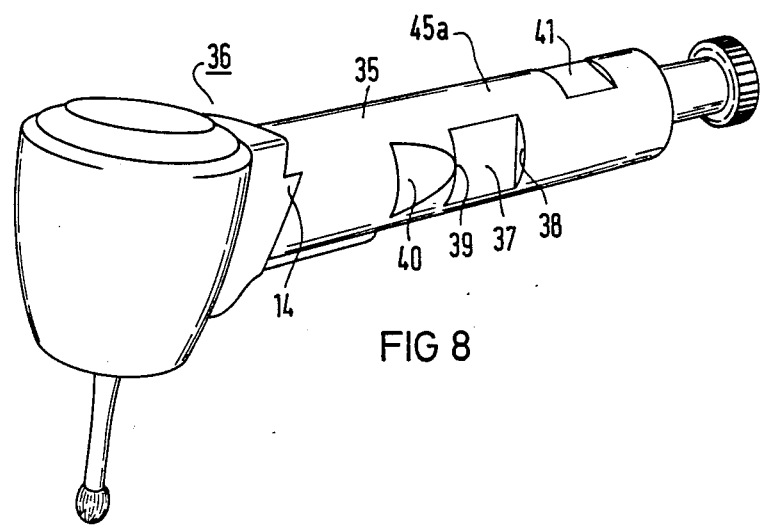
FIG. 8 is a perspective view of a second embodiment of the head part for use with a guide sleeve of FIG. 7.
Figure 9:
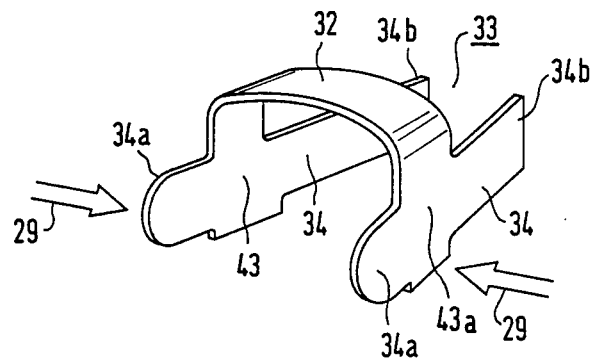
FIG. 9 is a perspective view of a second embodiment of a catch member for the head part.

An embodiment of the catch mechanism is illustrated in FIGS. 7, 8 and 9. In FIG. 7, a guide sleeve 30 is fashioned for the acceptance of a catch member 33 which is shown in greater detail in FIG. 9 and also for receiving a head part 36 shown in FIG. 8. On an upper surface, the guide sleeve 30 contains a turned portion 31 which forms a groove for receiving a shackle 32 of a catch member 33. The shackle 32 of the catch member 33 is in turn connected to lateral, resilient sections 34 whose one ends 34a form pressure faces for releasing the latching and whose other ends 34b form the engagement means or catch edges for the latching.

The sleeve 30, in addition to the groove 31, is provided with side apertures or clearances 42 adjacent the groove 31 with axially extending recesses or clearances 43. As illustrated, the recesses 43 form lateral slots in the sleeve 30 that are in communication with the bore 109 that receives a shank 35 of the head part 36.

The shank 35 of the head part 36 contain a first recess 37 on each side. The recess 37 forms a stop face or surface 38 and at the front of the recess 37, it has a tilting edge 39 that contains a second recess 40. In addition, the shank has a single third recess 41 on an upper surface.

For the assembly of the resilient catch member 33, it is inserted over the sleeve 30 with the shackle 32 being received in the groove 31. As this occurs, the two lateral resilient sections are received in the lateral slots formed by the clearance or aperture 43. As illustrated in FIG. 9, the two resilient sections 34 are arranged with the ends 34b converging towards each other. Thus, when they are inserted on the sleeve 30, the ends 34b will extend into the axially bore 109 of the sleeve. When the shank 35 of the head part 36 is axially introduced into the bore 109 of the guide sleeve 30, the end faces 34b of the resilient sections 34 will become seated against the two seating surfaces 38 of the recesses 37. In this position, the head part 36 is secured against axial disengagement. When the legs of the actuation element 9 are pressed radially together, this will act on the two ends 34a as indicated by the arrows 29. The resilient sections 34 have a portion 43a which becomes seated on a tilt edge or portion 39 of the head part 35. Given further pressure, the ends 34a pivot or move into the recesses 40 of the shank and the other ends 34b are pivoted out of the recess 37 and, therefore, out of engagement with the stop surfaces 38.

Figure 10:
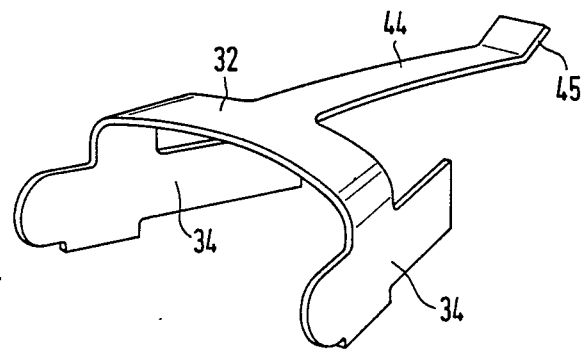
FIG. 10 is a perspective view of a modification of the second embodiment of the catch member of FIG. 9.

In order to achieve additional security against the head part 36 sliding unintentionally out even given inadvertant actuation of the actuator 9, the shackle 32 can be provided with a resilient continuation 44 as illustrated in FIG. 10. A free end 45 of the continuation 44 engages into the third recess 41 of the head part 36, but preferably not until a definite axial movement has occurred. The end 45 of the continuation thus, only comes into engagement when after release of the actuation latch, the head part has executed a slight axial stroke in the removal direction, for example, a movement lying in the region of 1 to 2 mm. Thus, when the ends 34b are engaged against the stop surfaces 38, the free end 45 will be engaged on a portion 45a of the shank 35 which is between the third recess 41 and the head but immediately adjacent the third recess.

A third embodiment of the catch mechanism is illustrated in FIGS. 11-14. In this embodiment, a guide sleeve 46 contains planar flattened portions 48 and 48a on both sides which respectively graduate by means of a perpendicular stop edge or shoulder 47. In addition, the sleeve has an aperture 53 in communication with an axial bore 110. Strip-shaped resilient elements 49, which are shown in FIGS. 12 and 13, are pressed against these flattened portions 48 and 48a when in the assembled position. The resilient element 49 contains a lateral shoulder 50 between the ends 49a and 49b and the shoulder 50 has radially inward directed first projections 51. The end 49b has radially inward second projection 52. With the element 49 assembled on the guide sleeve 46, the projection 51 will press against the shoulder 47 to secure the resilient element 49 against dislocation in an axial direction and the second projection 52 will extend radially through aperature 53 and into the bore 110. In this embodiment, the one end 49a of the resilient element 49 forms a pressure face for the actuation of the latching. The second projection 52 forms the engagement means or catch surface which presses against the stop surface 38 of the recess 37 of the shank 35 when it is received in the bore 110.

In the assembled condition, the two resilient elements 49 are held by means of a bow-shaped spring 54 (FIG. 14) which is inserted into a correspondingly turned out portion or groove 55 in the sleeve 46. Instead of a multipart construction for the catch element, it is also conceivable that the two resilient elements 49 and the bow 54 are constructed as a single piece.

Figure 6:
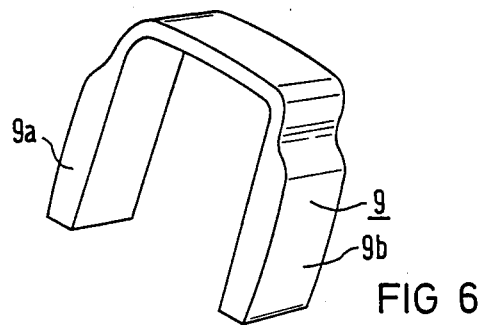
FIG. 6 is a perspective view of a first embodiment of an actuation member for the catch member of FIG. 5.

A fourth embodiment of the catch mechanism is shown by a head part 60 of FIG. 15 which coacts with a guide sleeve 70 of a grip piece or part. The head part 60 has a shank 61 which has a turned portion 62 that receives a sleeve 63 forming the catch member. The sleeve 63, as illustrated in FIG. 16, has a longitudinal slot 64 that extends the entire length and allows the sleeve to be slipped over the shank in a slightly expanded condition during assembly. This slot 64 can also be used in conjunction with a spline or key to secure the sleeve 63 against twisting. In addition, the sleeve has a plurality of slots 65 which extends only over a part of the sleeve's length and form resilient tabs 66 on both sides of the sleeve. The resilient tabs 66 have end surfaces or edges 67 which will engage stop surfaces 68 on two catch hooks 69 (FIG. 17) which are provided on a guide sleeve 70 when the shank 61 is inserted in a bore 111 of the sleeve 70. Except for the latching and arrangement of the actuation member, the guide sleeve 70 is substantially the same structure as the guide sleeves in FIGS. 4 and 7. The actuation member 71 (FIG. 18) has a U-shaped construction similar to the actuation element 9 of FIG. 6. However, it has, in addition, two retaining arms 71a on both sides which are inserted into longitudinally extending grooves 72 of the guide sleeve 70. The arms 71a are secured against falling out by means of a latching composed of a peg 73 that is received in a radial bore 74 of the guide sleeve. In contrast to the embodiment set forth hereinbefore, the latching element 71 lies directly against a slanted end face 75 of the guide sleeve 70. In the latched condition, the actuation element 71 will lie between the slant face 76 of the head part 60 and the slant face 75 of the guide sleeve 71. However, a face portion 77 of the guide sleeve 70 forms an axial stop for the two hand piece parts and is seated against the lower part of the end face 76 of the head part 60 when the two parts are latched together.

As in the previous embodiments, the shank 61 is provided with a projection or key 78 which is received in a slot 79 of the guide sleeve 70 when the parts are assembled to provide anti-twisting arrangement. It is especially advantageous to arrange the projection or key in the guide slot not on the under side but on an upper surface of the head part as indicated in FIGS. 15, 17 and 18 withtthe key 78′ in the slot 79′. When the gripping part with the guide sleeve 70 is assembled with the head part, a precise positioning, i.e. an alignment of the parts to be connected to one another which is suited to the function, can thus, be achieved. When the head part and the gripping part are twisted relative to one another and are not properly aligned to one another in accordance with their function then the slanted end face of the actuation element 71 will be seated against the catch nose or projection 78′ and slide along the projection until the projection engages in the slot 79′.

The anti-twist protection of the resilient sleeve 63 can be provided by an additional anti-twist pin or element provided at a head part of the shank 61 to be engaged in the slot 64. In addition, the projection or key 78 or 78′ can also be used.

In their nonlatched condition, the two resilient tabs 66 have their free ends spread slightly outwardly to project beyond the diameter of the shank 61. When the guide sleeve 70 is slipped on, the two catch hooks 69 will slide along the outside surface of the tab 66 and press them inwardly until their ends finally pass over the ends 67, then the ends 67 will spring outward to engage the stop surfaces 68 of the hooks 69. For unlatching, the actuation element 71 is pressed slightly inwardly at the two radial locations indicated by the arrows in FIG. 18 and the resilient tabs or strips 66 are thus, pressed into a clearance space 80 which is provided for this purpose on the shank 61 so that the head part 60 can be pulled axially from the gripping sleeve 5 or, respectively, from the guide sleeve 70.

In the embodiment of the catch member 63, which is illustrated in FIGS. 15 and 16, the sleeve has a constant cross section. An alternative to this, a catch sleeve 63a is illustrated in FIG. 19 and can be provided with resilient tabs which are not spread out in the nonlatching position but rather comprise catch noses 81 at their ends. These catch noses 81 are provided with an oblique run-on face.

With the embodiments of FIGS. 15–18, an additional protection against axially displacement of the head part, given a nonlatching of the parts, can be provided. Such additional latching protection can be composed of a leaf spring which is secured to the guide sleeve and has a free end that is provided with a catch nose which will engage into a notch provided in the shank 61. As already mentioned, such an additional protection is expediently arranged so that it does not take effect until the two hand piece parts have moved a slight axial distance in the direction of disassembly.

Although various minor modifications may be suggested by those versed in the art, it should be understood that we wish to embody with the scope of the patent granted hereon, all such modifications as reasonably and properly come within the scope of our contribution to the art.

We claim:

1. A catch mechanism for releasably connecting a head part to a gripping part of a dental handpiece, said head part having a head housing with a neck having a shank, said gripping part containing a guide sleeve with an axial bore for receiving the shank, said shank and guide sleeve having coacting anti-twist elements to prevent relative rotation therebetween, said catch mechanism including one of said head part and gripping part having at least one stop surface, the other of said head part and gripping part having a catch member for each stop surface movable radially from a first position engaging said stop surface to a second position disengaged from said stop surface to disengage the latching connection, and a separate actuation element being carried on the gripping part adjacent the head housing having a portion moving radially relative to the guide sleeve and shank to shift the catch member to the second position to disengage the stop surface.

2. A catch mechanism according to claim 1, wherein the catch member is formed by at least two elements which extend essentially parallel to an axis of said shank, each of said elements having an end face pressing against a stop surface when the elements are in the first position.

3. A catch mechanism according to claim 2, wherein said catch elements are mounted on the shank of the head part with said end faces directed toward the head part and projecting radially outward beyond the diameter of the shank, said cooperating stop surfaces being provided on two catch hooks which are provided on an end of the guide sleeve, said shank being provided with a recess adjacent each end of the catch elements so that the ends of the elements can be moved to the second position to disengage the stop surfaces, said actuation element being positioned adjacent the two catch hooks to apply a radial force to the ends of the catch elements to shift the ends into the recesses of said shank to enable disassembly of the parts.

4. A catch mechanism according to claim 3, wherein the catch member is composed of a sleeve having a longitudinally extended slot so that it can be resiliently inserted onto the shank, said sleeve having a plurality of additional slots extending from one end for part of the length to form said catch elements.

5. A catch mechanism according to claim 1, wherein the catch member is accepted on the guide sleeve and held in an anti-twisting fashion in the gripping part.

6. A catch mechanism according to claim 1, wherein the catch member comprises a radially acting engagement means arranged on the gripping part of the handpiece.

7. A catch mechanism according to claim 6, wherein the catch member is formed of two elements which extend essentially parallel to an axis of the guide sleeve, said shank having two stop surfaces and each element having an end face pressing against the stop surface while in the latched condition.

8. A catch mechanism according to claim 6, wherein the catch member has two parallel extending resilient elements and a shackle having semi-circular configuration of about half the shank's circumference, one end of said resilient elements forming a pressure face for the actuation element.

9. A catch mechanism according to claim 8, wherein the shackle is resiliently fashioned and forms the engagement edge of the catch member, said shank having a catch nose containing the stop surface which is engaged by the shackle when in the latching condition.

10. A catch mechanism according to claim 9, wherein clearances are provided on the guide sleeve adjacent the pressure faces of the resilient elements and the resilient elements have the other ends received in a recess of the guide sleeve.

11. A catch mechanism according to claim 10, wherein the other end of the resilient elements have apertures, said guide sleeve having pegs for insertion into the apertures to hold the elements in the recesses of the guide sleeve.

12. A catch mechanism according to claim 6, wherein the shank has a pair of first recesses forming a pair of stop surfaces and wherein the catch member comprises two resilient elements extending substantially parallel to an axis of the guide sleeve, said resilient elements being mounted on the guide sleeve with one end of each element extending into the bore of the sleeve for engagement with the pair of stop surfaces of said shank.

13. A catch mechanism according to claim 12, wherein the resilient elements are mounted on the guide sleeve with the one end converging radially inward.

14. A catch mechanism according to claim 12, wherein the shank member includes a second recess adjacent each of the first recesses, said second recess forming a tilt angle with the first recess and forming a clearance for receiving the resilient element when the resilient elements are moved to the second position.

15. A catch mechanism according to claim 6, wherein the catch member is formed by two spring elements which extend essentially parallel to the axis of the guide sleeve and are held by a shackle arranged over approximately half the circumference of the shank, said shackle having a resilient continuation extending in the axial direction and providing a catch nose at its free end, said shank having a third recess for receiving said catch nose to form a second latching arrangement to prevent disassembly.

16. A catch mechanism according to claim 15, wherein the position of the third recess relative to the catch nose is selected so that the catch nose is not received in said third recess until the parts have moved a short distance in the direction of disassembly.

17. A catch mechanism according to claim 6, wherein said guide sleeve has a semi-circular groove in an outer surface, said groove terminating in apertures, wherein the catch member comprises two spring elements being positioned on the guide sleeve to extend substantially parallel to the axis of the guide sleeve with an end extending radially inward at each aperture by a semi-circular shackle element portion being received in said groove.

18. A catch mechanism according to claim 6, wherein the catch member has two resilient elements mounted on the guide sleeve to extend parallel to the bore, said resilient elements having lateral shoulders having first projections extending radially inward, each of said elements having second projections adjacent one end extending radially inwardly, said guide sleeve having a shoulder on each side for engagement with said first projections to prevent axial shifting of the elements on said sleeve and said guide sleeve having apertures adjacent the second projections through which the second projections extend into the bore for engagement on stop surfaces provided on said shank.

19. A catch mechanism according to claim 18, wherein the guide sleeve is provided with planar flat surfaces adjacent each of the shoulders, said resilient elements being held on said flat surfaces by a U-shaped shackle assembled on said guide sleeve.

20. A catch mechanism according to claim 1, wherein the actuation element is a U-shaped resilient part having a pair of legs, said legs forming actuation keys for engaging the catch members.

21. A catch mechanism according to claim 20, wherein the actuation member is received in a circumferential recess in the guide sleeve with only the two actuation keys projecting from opposite surfaces of the handpiece.

22. A catch mechanism according to claim 20, wherein the actuation element is composed of a resilient plastic.

23. A catch mechanism according to claim 20, wherein the actuation element has retaining parts extending from both legs in an axial direction, said retaining parts being received in recesses formed in the guide sleeve to hold said actuation element on said guide sleeve.

24. A catch mechanism according to claim 1, wherein an end surface of the gripping part engages on an end surface on the head part, said end surfaces each extending oblique to the axis of the guide sleeve with a portion of the end surfaces closest to the head housing being adjacent the tool.

* * * * *